(12) United States Patent
Fujii et al.

(10) Patent No.: US 8,415,098 B2
(45) Date of Patent: Apr. 9, 2013

(54) METHOD FOR ISOLATING SPECIFIC GENOMIC REGIONS

(75) Inventors: Hodaka Fujii, Osaka (JP); Toshitsugu Fujita, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/390,170

(22) PCT Filed: Aug. 20, 2010

(86) PCT No.: PCT/JP2010/064052
§ 371 (c)(1),
(2), (4) Date: Mar. 15, 2012

(87) PCT Pub. No.: WO2011/021684
PCT Pub. Date: Feb. 24, 2011

(65) Prior Publication Data
US 2012/0164689 A1  Jun. 28, 2012

(30) Foreign Application Priority Data
Aug. 21, 2009 (JP) .................... 2009-191762

(51) Int. Cl.
C12Q 1/68 (2006.01)
C07H 21/04 (2006.01)
C12N 15/63 (2006.01)

(52) U.S. Cl. ..... 435/6; 536/23.1; 536/24.31; 536/24.33; 435/320.1

(58) Field of Classification Search .................... None
See application file for complete search history.

(56) References Cited

U.S. PATENT DOCUMENTS
2007/0196843 A1   8/2007   Green et al.

FOREIGN PATENT DOCUMENTS
JP   2009-519039   5/2009

OTHER PUBLICATIONS

English translation of the International Preliminary Report on Patentability and Written Opinion dated Mar. 13, 2012.
International Search Report issued Nov. 22, 2010 in International (PCT) Application No. PCT/JP2010/064052.
M. Simonis et al., "An Evaluation of 3C-Based Methods to Capture DNA Interactions", Nature Methods, vol. 4, No. 11, pp. 895-901, Nov. 2007.
J. Dekker et al., "Capturing Chromosome Conformation", Science, vol. 295, No. 5558, pp. 1306-1311, 2002.
J. Dejardin et al., "Purification of Proteins Associated with Specific Genomic Loci", Cell, vol. 136, No. 1, pp. 175-186, Jan. 9, 2009.
M. Simonis et al., "Nuclear Organization of Active and Inactive Chromatin Domains Uncovered by Chromosome Conformation Capture-on-Chip (4C)", Nature Genetics, vol. 38, No. 11, pp. 1348-1354, 2006.
A. Hoshino et al., "Insertional Chromatin Immunoprecipitation: A Method for Isolating Specific Genomic Regions", Journal of Bioscience and Bioengineering, vol. 108, No. 5, pp. 446-449, Nov. 2009.
H. Fujii et al., "Novel Reporter Cell Line to Analyze Cytokine-Mediated Expression Regulation of c-myc Gene", Journal of Bioscience and Bioengineering, vol. 108, No. 5, pp. 438-440, 2009.
M. J. Solomon et al., "Mapping Protein-DNA Interactions In Vivo with Formaldehyde: Evidence that Histone H4 is Retained on a Highly Transcribed Gene", Cell, vol. 53, pp. 937-947, Jun. 17, 1988.
M. J. Solomon et al., "Formaldehyde-Mediated DNA-Protein Crosslinking: A Probe for In Vivo Chromatin Structures", Proc. Natl. Acad. Sci. USA, vol. 82, pp. 6470-6474, Oct. 1985.
J. Griesenbeck et al., "Affinity Purification of Specific Chromatin Segments from Chromosomal Loci in Yeast", Molecular and Cellular Biology, vol. 23, No. 24, pp. 9275-9282, Dec. 2003.
A. Hoshino et al., "Inducible Translocation Trap: A System for Detecting Inducible Nuclear Translocation", Molecular Cell, vol. 15, pp. 153-159, Jul. 2, 2004.
T. Fujita et al., "Insertional Chromatin Immunoprecipitation: A Method for Isolating Specific Genomic Regions that retain in Vivo Chromatin Structure", Poster Presentation, The 32nd Annual Meeting of the Molecular Biology Society of Japan, Dec. 11, 2009.

*Primary Examiner* — Amy Bowman
(74) *Attorney, Agent, or Firm* — Wenderoth, Lind & Ponack, L.L.P.

(57) ABSTRACT

Provided is a method for specifically isolating any genomic region while maintaining interaction of the genomic region with its interacting molecule(s). According to the method comprising the following steps 1 to 5:

Step 1:
  preparing a cell in which a DNA fragment having a recognition sequence(s) for an exogenous DNA-binding molecule is inserted in genomic DNA of a genomic region to be isolated;
Step 2:
  bringing genomic DNA of the cell into contact with an exogenous molecule at least having a DNA-binding domain of the exogenous DNA-binding molecule;
Step 3:
  performing a treatment for maintaining interaction of the genomic DNA of the cell with a molecule(s) interacting with the genomic DNA;
Step 4:
  performing a treatment for fragmenting the genomic DNA; and
Step 5:
  allowing a complex to be formed by binding of a molecule capable of specifically binding to the exogenous molecule, and then collecting the complex,
specific genomic regions can be specifically isolated while kept interacting with their interacting molecules.

14 Claims, 7 Drawing Sheets

LexA-element IRF-1 promoter GFP reporter (LIPG)

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Primer Sequence

<400> SEQUENCE: 1
ccctttcctg agggaatgaa agcgttaacg                                  30

<210> SEQ ID NO 2
<211> LENGTH: 30
<212> TYPE: DNA
<213> ORGANISM: Artificial Sequence
<220> FEATURE:
<223> OTHER INFORMATION: Primer Sequence

<400> SEQUENCE: 2
```

```
tgcggccgct tagggttcac cggcagccac                                             30

<210> SEQ ID NO 3
<211> LENGTH: 22
<212> TYPE: DNA
<213> ORGANISM: Artificial Sequence
<220> FEATURE:
<223> OTHER INFORMATION: Primer Sequence

<400> SEQUENCE: 3
ccccagtgca agtgcaggtg cc                                                     22

<210> SEQ ID NO 4
<211> LENGTH: 22
<212> TYPE: DNA
<213> ORGANISM: Artificial Sequence
<220> FEATURE:
<223> OTHER INFORMATION: Primer Sequence

<400> SEQUENCE: 4
cgtcgccgtc cagctcgacc ag                                                     22

<210> SEQ ID NO 5
<211> LENGTH: 24
<212> TYPE: DNA
<213> ORGANISM: Artificial Sequence
<220> FEATURE:
<223> OTHER INFORMATION: Primer Sequence

<400> SEQUENCE: 5
tgtacttccc cttcgccgct agct                                                   24

<210> SEQ ID NO 6
<211> LENGTH: 24
<212> TYPE: DNA
<213> ORGANISM: Artificial Sequence
<220> FEATURE:
<223> OTHER INFORMATION: Primer Sequence

<400> SEQUENCE: 6
gcaatccaaa cacttagcgg gatt                                                   24

<210> SEQ ID NO 7
<211> LENGTH: 22
<212> TYPE: DNA
<213> ORGANISM: Artificial Sequence
<220> FEATURE:
<223> OTHER INFORMATION: Primer Sequence

<400> SEQUENCE: 7
ttctctatcg ataggtacct cg                                                     22

<210> SEQ ID NO 8
<211> LENGTH: 22
<212> TYPE: DNA
<213> ORGANISM: Artificial Sequence
<220> FEATURE:
<223> OTHER INFORMATION: Primer Sequence

<400> SEQUENCE: 8
tctattcagc ggatctcgag cg                                                     22
```

METHOD FOR ISOLATING SPECIFIC GENOMIC REGIONS

This application is a U.S. national stage of International Application No. PCT/W2010/064052 filed Aug. 20, 2010.

TECHNICAL FIELD

The present invention relates to a method for isolating a specific genomic region, and in particular, to a method for isolating a specific genomic region while maintaining interaction of the specific genomic region with its interacting molecule(s).

BACKGROUND ART

Biochemical and molecular biological analysis of chromatin domains is critical for understanding of molecular mechanisms of epigenetic regulation. However, the biochemical characteristics of chromatin domains are poorly understood. This is because sampling methods applicable to biochemical and molecular biological analysis of chromatin domains are limited.

The biochemical and molecular biological analysis of chromatin domains requires a sample retaining interaction of genomic DNA and its interacting molecule(s). As a method for isolating a specific genomic region while maintaining interaction of the specific genomic region with its interacting molecule(s), the following examples are known.

(1) Chromatin Immunoprecipitation

Chromatin immunoprecipitation (hereinafter referred to as "ChIP") is a method involving immunoprecipitation of a specific genomic region with an antibody against a known DNA-binding protein for isolation of the region concerned (see Non Patent Literature 1 and 2). Therefore, there is limitation that ChIP cannot be used without the data regarding DNA-binding proteins. In addition, since DNA-binding proteins generally bind to plural regions of genomic DNA and the resulting immunoprecipitates contain various genomic regions, ChIP has difficulty in isolation of a single specific genomic region. Further, ChIP does not enable isolation of a genomic region to which known DNA-binding proteins do not bind.

(2) Chromosome Conformation Capture (Hereinafter Referred to as "3C")

3C or its derivatives can be used for identification of a genomic region(s) interacting with a specific genomic region(s) (see Non Patent Literature 3 to 5). However, 3C involves an enzymatic reaction with restriction enzymes or ligases under non-optimal conditions, namely crosslinking conditions, and therefore has a high possibility of detecting unphysiological interactions. In addition, since restriction enzyme digestion is likely to be incomplete under crosslinking conditions, amplification of neighboring regions of the target genomic region is unavoidable in PCR, resulting in an extremely high background, which makes it difficult to detect unidentified interactions.

(3) Fluorescence In Situ Hybridization (Hereinafter Referred to as "FISH")

FISH alone or in combination with immunofluorescence can be used to detect interaction of a specific genomic region with other genomic regions, RNA and proteins. However, this method has a low resolution and cannot be used for detection of interaction with unidentified molecules.

(4) Proteomics of Isolated Chromatin Segments (Hereinafter Referred to as "PICh")

PICh utilizes a specific nucleic acid probe for isolation of a specific genomic region, and it is reported that this method enables isolation of telomeric regions having multiple repeats of a sequence complementary to the probe (see Non Patent Literature 6). Regarding PICh, which involves annealing of a nucleic acid probe and a target genomic region under crosslinking conditions, it is not reported whether a low copy number or one copy of a specific genomic region can be isolated.

(5) Method of Non Patent Literature 7

In Non Patent Literature 7, an attempt to isolate a specific genomic region by affinity purification is described. In this attempt, the cell used is yeast and application to higher eukaryotic cells is yet to be tested. In this method, the specific genomic region is cut out with the aid of the Cre-loxP system, and this procedure may alter chromatin structures. In addition, due to lack of crosslinking treatment with formaldehyde, molecules bound to the specific genomic region, such as proteins and DNA, may dissociate in a purification process.

[Citation List]
[Non Patent Literature]

Non Patent Literature 1:
Solomon, M. J., Larsen, P. L., Varshaysky, A., Mapping protein-DNA interactions in vivo with formaldehyde: evidence that histone H4 is retained on a highly transcribed gene. Cell (1988) 53, 937-947

Non Patent Literature 2:
Solomon, M. J., Varshaysky, A., Formaldehyde-mediated DNA-protein crosslinking: a probe for in vivo chromatin structures. Proc. Natl. Acad. Sci. USA (1985) 82, 6470-6474

Non Patent Literature 3:
Dekker, J., Rippe, K., Dekker, M., and Kleckner, N. Capturing chromosome conformation. Science (2002) 295, 1306-1311

Non Patent Literature 4:
Simonis, M., Klous, P., Splinter, E., Moshkin, Y., Willemsen, R., de Wit, E., van Steensel, B., and de Laat, W. Nuclear organization of active and inactive chromatin domains uncovered by chromosome conformation capture-on-chip (4C). Nat. Genet. (2006) 38, 1348-1354

Non Patent Literature 5:
Simonis, M., Kooren, J., and de Laat, W. An evaluation of 3C-based methods to capture DNA interactions. Nat. Methods (2007) 4, 895-901

Non Patent Literature 6:
Dejardin, J., and Kingston, R. E. Purification of proteins associated with specific genomic loci. Cell (2009) 136, 175-186

Non Patent Literature 7:
Griesenbeck, J., Boeger, H., Strattan, J. S., and Kornberg, R. D. Affinity purification of specific chromatin segments from chromosomal loci in yeast. Mol. Cell Biol. (2003) 23, 9275-9282

SUMMARY OF INVENTION

Technical Problem

Since various problems as described above are present in the conventional methods for isolating a specific genomic region while maintaining interaction of the specific genomic region with its interacting molecule(s), development of a novel method which solves these problems and ensures provision of a material suitable for biochemical and molecular biological analysis of chromatin domains has been desired.

Accordingly, an object of the present invention is to provide a method for specifically isolating any genomic region while maintaining interaction of the genomic region with its interacting molecule(s).

Solution to Problem

The present invention includes the following as a solution to the above-mentioned problems.

[1] A method for isolating a specific genomic region while maintaining interaction of the specific genomic region with its interacting molecule(s), the method comprising the steps 1 to 5:

Step 1:
preparing a cell in which a DNA fragment having a recognition sequence(s) for an exogenous DNA-binding molecule is inserted in genomic DNA of a genomic region to be isolated;

Step 2:
bringing genomic DNA of the cell into contact with an exogenous molecule at least having a DNA-binding domain of the exogenous DNA-binding molecule;

Step 3:
performing a treatment for maintaining interaction of the genomic DNA of the cell with a molecule(s) interacting with the genomic DNA;

Step 4:
performing a treatment for fragmenting the genomic DNA; and

Step 5:
allowing a complex to be formed by binding of a molecule capable of specifically binding to the exogenous molecule, and then collecting the complex.

[2] The method, according to the above [1], wherein the exogenous DNA-binding molecule is an exogenous DNA-binding protein or an exogenous nucleic acid.

[3] The method according to the above [1] or [2], wherein the exogenous molecule is a fusion molecule having a tag sequence(s).

[4] The method according to the above [3], wherein the fusion molecule has two kinds of tag sequences linked to each other via a protease recognition sequence.

[5] The method according to any of the above [1] to [4], wherein the exogenous molecule is a fusion molecule having a nuclear localization signal(s).

[6] The method according to any of the above [1] to [5], wherein the DNA fragment having a recognition sequence(s) for an exogenous DNA-binding molecule is inserted into the genomic DNA by homologous recombination in step 1.

[7] The method according to any of the above [1] to [5], wherein a DNA fragment having a recognition sequence(s) for an exogenous DNA-binding molecule and a DNA sequence(s) of a specific genomic region is introduced into a cell in step 1.

[8] The method according to any of the above [1] to [7], wherein, in step 2, a gene encoding the exogenous molecule is introduced into the cell prepared in step 1, for expression of the gene in the cell.

[9] The method according to any of the above [1] to [8], wherein the treatment for maintaining the interaction is crosslinking.

[10] The method according to any of the above [1] to [9], wherein the treatment for fragmenting the genomic DNA is restriction enzyme treatment, partial degradation treatment with deoxyribonuclease, or sonication.

[11] A kit for isolating a specific genomic region, comprising a targeting vector for inserting, into genomic DNA, a DNA fragment having a recognition sequence(s) for an exogenous DNA-binding molecule.

[12] A kit for isolating a specific genomic region, comprising a vector for introducing, into a cell, a DNA fragment having a recognition sequence(s) for an exogenous DNA-binding molecule and a DNA sequence(s) of a specific genomic region.

[13] The kit according to the above [12], wherein the DNA fragment further has a reporter gene.

[14] The kit according to any of the above [11] to [13], further comprising an exogenous molecule at least having a DNA-binding domain of the exogenous DNA-binding molecule, or an expression vector for the exogenous molecule.

Advantageous Effects of Invention

According to the present invention, any genomic region can be specifically isolated while kept interacting with its interacting molecule(s). Since the isolated genomic region is kept interacting with its interacting molecule(s), this genomic region is very useful as a sample for the analysis of molecular mechanisms of epigenetic regulation.

DESCRIPTION OF EMBODIMENTS

<Method for Isolating a Specific Genomic Region>

The method for isolating a specific genomic region according to the present invention (hereinafter referred to as "the method of the present invention") at least comprises steps 1 to 5 described below:

Step 1:
preparing a cell in which a DNA fragment having a recognition sequence(s) for an exogenous DNA-binding molecule is inserted in genomic DNA of a genomic region to be isolated;

Step 2:
bringing genomic DNA of the cell into contact with an exogenous molecule at least having a DNA-binding domain of the exogenous DNA-binding molecule;

Step 3:
performing a treatment for maintaining interaction of the genomic DNA of the cell with a molecule(s) interacting with the genomic DNA;

Step 4:
performing a treatment for fragmenting the genomic DNA; and

Step 5:
allowing a complex to be formed by binding of a molecule capable of specifically binding to the exogenous molecule, and then collecting the complex.

The method of the present invention enables isolation of a specific genomic region while maintaining interaction of the specific genomic region with its interacting molecule(s). As long as a specific genomic region can be isolated while kept interacting with its interacting molecule(s), the method may comprise a step(s) other than steps 1 to 5, and the details of the step(s) are not limited.

Hereinafter, the method of the present invention will be described in detail in the order of the steps.

(1) Step 1

Step 1 is a step of preparing a cell in which a DNA fragment having a recognition sequence(s) for an exogenous DNA-binding molecule is inserted in genomic DNA of a genomic region to be isolated. The kind of the cell is not particularly limited, and both of prokaryotic cells and eukaryotic cells can be preferably used. As the genomic region to be isolated, any genomic region can be selected. The method for inserting, into the genomic DNA, a DNA fragment having a recognition sequence(s) for an exogenous DNA-binding molecule can be selected from known methods. For example, homologous recombination etc. can be used. Homologous recombination can be easily performed, for example, by use of a recombineering method (Copeland, N. G., Jenkins, N. A., Court, D. L. Recombineering: a powerful new tool for mouse functional genomics. Nat. Rev. Genet. (2001) 2, 769-779). Since homologous recombination allows insertion of a DNA fragment having a recognition sequence(s) for an exogenous DNA-binding molecule into any site in the genomic DNA, selection of the genomic region to be isolated has no limitations and any genomic region can be selected. In this respect, the method of the present invention is very useful as compared with conventional methods.

It is also possible to prepare a transgene by isolating a genomic region to be analyzed and inserting thereinto a recognition sequence(s) for an exogenous DNA-binding molecule and to introduce the transgene into cells. In this case, although the isolated genomic region is destined to be inserted into a locus different from its original locus, useful data is obtainable as long as the transgene has a minimal region required for expression of functions such as regulation of gene expression.

Introduction of the above-mentioned transgene into cells is performed, for example, as follows. A DNA fragment having a recognition sequence(s) for an exogenous DNA-binding molecule and a DNA sequence(s) of a specific genomic region (transgene) is prepared, and the DNA fragment is then introduced into cells in step 1. The recognition sequence(s) for an exogenous DNA-binding molecule may be inserted within or in the vicinity of the specific genomic region. The prepared transgene is introduced into cells by use of a known gene transfer method, and a cell having the transgene integrated in the genome is selected. Integration of the transgene in the genome can be easily confirmed by, for example, using the transgene further having a marker gene.

The exogenous DNA-binding molecule is not particularly limited as long as it is an exogenous molecule capable of binding to a specific DNA. For example, an exogenous DNA-binding protein, an exogenous nucleic acid, etc. can be preferably used.

The exogenous DNA-binding protein can be appropriately selected from known DNA-binding proteins. It is particularly preferable that an exogenous DNA-binding protein whose binding recognition sequence is absent in the genomic DNA of a cell to be used is selected, but an exogenous DNA-binding protein whose binding recognition sequence is infrequently present in the genomic DNA may be also selected. It is also possible to artificially design a protein or a peptide whose binding recognition sequence is absent in the genomic DNA of a cell to be used. The data on the recognition sequence for an exogenous DNA-binding protein to be used can be easily obtained from known literature etc.

Examples of eukaryotic DNA-binding proteins include p53, Jun, Fos, GCN4 and GAL4. Examples of prokaryotic DNA-binding proteins include a LexA repressor (hereinafter referred to as "LexA"), a P22 Arc repressor, MetJ, CENP-B, Rap1, Xy1S/Ada/AraC, Bir5 and DtxR. Phage-derived lambda cI protein etc. can be also used.

The exogenous nucleic acid can be obtained, for example, by affinity purification of a molecular species capable of binding to a target genomic DNA sequence from a random nucleic acid sequence library, followed by enrichment and selection by use of PCR etc. Into such a selected nucleic acid, a suitable mutation may be introduced to increase the affinity for the target genomic DNA sequence.

The DNA fragment having a recognition sequence(s) for an exogenous DNA-binding molecule has a recognition sequence at least, and preferably has several repeats of a recognition sequence. Several repetitions of a recognition sequence can significantly increase the probability that an exogenous DNA-binding molecule recognizes the recognition sequence and thereby binds thereto. In the case of introduction of a specific genomic region as a transgene into cells, a transgene having several repeats of the specific genomic region may be also used.

(2) Step 2

Step 2 is a step of bringing genomic DNA of the cell prepared in step 1 into contact with an exogenous molecule at least having a DNA-binding domain of the exogenous DNA-binding molecule. The exogenous molecule used in step 2 may be any exogenous molecule capable of binding to the recognition sequence inserted into the genomic DNA in step 1. Preferred is such an exogenous molecule that a molecule capable of specifically binding thereto (for example, antibody) is easily obtainable. Thus, as the exogenous molecule, a whole exogenous DNA-binding molecule capable of binding to the recognition sequence, a molecule having a DNA-binding domain of an exogenous DNA-binding molecule capable of binding to the recognition sequence, or a fusion molecule thereof with another molecule(s) can be preferably used.

In the case where the exogenous DNA-binding molecule is an exogenous DNA-binding protein, a full-length exogenous DNA-binding protein capable of binding to the recognition sequence, a partial protein having a DNA-binding domain of an exogenous DNA-binding protein capable of binding to the recognition sequence, or a fusion protein thereof with another protein(s) can be preferably used as the exogenous molecule.

In the case of the fusion molecule, a fusion partner molecule is preferably a tag sequence(s). Such a fusion molecule with a tag sequence(s) can bind to the recognition sequence inserted in the genomic DNA and a molecule capable of specifically binding to the fusion molecule is easily obtainable. The tag sequence is not particularly limited and can be appropriately selected from known tag sequences. Specific examples of the tag sequence include a histidine tag, a FLAG tag, a Strep tag, a calmodulin-binding peptide, a GST tag and an MBP tag.

The fusion molecule with a tag sequence(s) may be also designed to have two kinds of tag sequences linked to each other via a protease recognition sequence. In this case, since the genomic region bound to the fusion molecule can be purified in two steps, the background due to nonspecific binding can be significantly reduced and the efficiency of specific isolation of specific genomic regions is significantly improved.

The protease recognition sequence via which two kinds of tag sequences are linked to each other can be appropriately selected from sequences recognizable by proteases usually used for separation of tag sequences. Known as a protease used for separation of tag sequences are, for example, Tobacco etch virus (TEV) protease, human rhinovirus (HRV) protease, enterokinase (EK), thrombin (Tb) and Factor Xa.

In the case where eukaryotic cells are used, the fusion molecule preferably has a nuclear localization signal(s). The fusion molecule having a nuclear localization signal(s) can enter into the nucleus and come into contact with the genomic DNA. The nuclear localization signal can be appropriately selected from known nuclear localization signals. Specific examples of the nuclear localization signal include the nuclear localization signal of SV40 T antigen, the nuclear localization signal of c-Myc, the nuclear localization signal of p53, and the nuclear localization signal of NF-κB p50. The fusion molecule may have an amino acid sequence(s) that is a cell-permeable motif (protein transduction domain).

In the case where the exogenous molecule used in step 2 is an exogenous protein, the exogenous protein can be produced, for example, as a recombinant protein by a known recombinant technique, that is, by inserting a DNA encoding the exogenous protein into a known expression vector, introducing the resulting expression vector into an appropriate host cell for expression of the protein, and purifying the expressed protein by a known method. In the case where the exogenous protein is a fusion protein, for example, DNAs each encoding a different constituent protein of the fusion protein are appropriately ligated to each other for preparation of a fusion DNA, and the fusion DNA is inserted into an expression vector.

In the case where the exogenous molecule used in step 2 is an exogenous nucleic acid, the exogenous nucleic acid can be produced by, for example, a known chemical synthesis, PCR, in vitro transcription, reverse transcription, transcription from integrated genes in cells, etc. In the case where the exogenous nucleic acid is a fusion molecule, it can be prepared by a known chemical synthesis.

The method for bringing genomic DNA of the cell prepared in step 1 into contact with an exogenous molecule is not particularly limited. For example, an exogenous protein or nucleic acid obtainable as described above by a known recombinant technique etc., is introduced into the cell prepared in step 1 by microinjection, electroporation, lipofection, etc. As the exogenous molecule, the above-mentioned fusion molecule having an amino acid sequence(s) that is a cell-permeable motif (protein transduction domain) can be also used for direct introduction into the cell prepared in step 1. It is also possible to, apart from the exogenous molecule, prepare a protein transduction domain fused with an amino acid sequence capable of binding to the exogenous molecule and to introduce a mixture of such a protein transduction domain and the exogenous molecule into the cell prepared in step 1. In the case where the cell prepared in step 1 is a eukaryotic cell, a fusion molecule having a nuclear localization signal(s) is used.

The exogenous molecule may be also expressed in the cell. In this case, the cell prepared in step 1 is used as a host cell, and an expression vector that can express the exogenous molecule in the cell is prepared and then introduced into the cell. In the case where the host is a prokaryotic cell, the expressed exogenous molecule can come into contact with the genomic DNA in the cytoplasm. In the case where the host is a eukaryotic cell, a fusion molecule having a nuclear localization signal(s) is used as the exogenous molecule for expression of the exogenous molecule so that the expressed exogenous molecule can enter into the nucleus from the cytoplasm and come into contact with the genomic DNA.

(3) Step 3

Step 3 is a step of performing a treatment for maintaining interaction of the genomic DNA of the cell prepared in step 1 with a molecule(s) interacting with the genomic DNA. With the genomic DNA, DNA-binding proteins such as transcription factors, nucleic acids such as DNA and RNA, other molecules, etc. are interacting depending on the stage of the cell. In addition, the exogenous molecule brought into contact in step 2 is bound to the recognition sequence for the exogenous DNA-binding molecule in the genomic DNA. In step 3, a treatment for maintaining interaction of the genomic DNA with such molecules is performed. Before this treatment, stimulation may be given to the cell if needed.

The treatment for maintaining the interaction is not particularly limited, but preferably, the maintained interaction is cancelable if needed so that separation and purification of interacting molecules for subsequent analysis can be performed. Preferable examples of the treatment include crosslinking. Preferable examples of an agent used for the crosslinking include formaldehyde.

(4) Step 4

Step 4 is a step of performing a treatment for fragmenting the genomic DNA. That is, the genomic DNA subjected to the treatment for maintaining interaction with its interacting molecule(s) in step 3 is cleaved into fragments in an appropriate size enough to contain an objective genomic region. For efficient fragmentation, it is preferable that cell lysis, cell disruption or chromatin fraction extraction is performed according to a known method before fragmentation.

Examples of the method for fragmentation include digestion of the genomic DNA with a restriction enzyme(s), partial degradation (partial cleavage) of the genomic DNA with deoxyribonuclease (endonuclease), and physical cleavage of the genomic DNA by sonication.

In the case where a restriction enzyme(s) is used, it is preferable to select a restriction enzyme(s) whose recognition sequence is absent within the genomic region to be isolated but is present in such a site that the digested fragment has as little as possible of a region other than the objective genomic region.

In the case where deoxyribonuclease (endonuclease) is used, it is preferable to determine in advance the reaction conditions which allow cleavage into fragments slightly larger than the size of the genomic region to be isolated.

In the case of sonication, it is preferable to determine in advance the treatment conditions which allow cleavage into fragments slightly larger than the size of the genomic region to be isolated.

(5) Step 5

Step 5 is a step of allowing a complex to be formed by binding of a molecule capable of specifically binding to the exogenous molecule, and then collecting the complex. Since the exogenous molecule is bound to the genomic DNA, specifically to the recognition sequence for the exogenous DNA-binding molecule in the genomic region to be isolated, and this binding (interaction) is maintained as a result of the treatment of step 3, the objective specific genomic region is contained in the complex formed by binding of a molecule capable of specifically binding to the exogenous molecule. Therefore, the objective specific genomic region can be isolated by collecting the formed complex.

The method used in step 5 may be any method that enables formation of a complex of the objective specific genomic region bound to the exogenous molecule and a molecule capable of specifically binding to the exogenous molecule, and subsequent collection of the complex. For example, the complex can be collected after precipitated by use of a carrier onto which an antibody or a peptide capable of specifically binding to the exogenous molecule, a nickel ion, etc. has been immobilized.

In the case where a fusion molecule having two kinds of tag sequences linked to each other via a protease recognition sequence is used as the exogenous molecule, the following procedures are preferable. The fusion molecule-genomic region complex is made to bind to a molecule capable of specifically binding to a first tag sequence, for formation of a first complex, and then the first complex is treated with protease for separation of the protease recognition sequence. Then, the genomic DNA-containing portion separated from the first complex is made to bind to a molecule capable of specifically binding to a second tag sequence, for formation of a second complex. Since the complex is purified in two steps, undesired concentration of molecules as a background due to nonspecific bindings to a molecule capable of specifically binding to the first tag sequence, and nonspecific bindings to a carrier onto which the molecule has been immobilized is avoidable. Therefore, the efficiency of specific isolation of specific genomic regions is significantly improved.

Alternatively, without using protease, by excessive addition of a molecule specifically competing with a tag sequence to release a complex containing a tagged exogenous molecule from a carrier onto which a molecule capable of specifically binding to the tagged exogenous molecule has been immobilized, the background can be reduced. Specifically, this can be done, for example, by addition of FLAG peptide to release a complex containing a FLAG-tagged DNA-binding molecule from a carrier onto which a molecule capable of specifically binding to the FLAG-tagged DNA-binding molecule has been immobilized.

<Use of the Isolated Specific Genomic Region(s)>

The specific genomic region isolated by the method of the present invention is very useful as a sample for the analysis of molecular mechanisms of epigenetic regulation. Since the interaction of the genomic DNA and molecules interacting therewith (proteins, DNA, RNA, etc.) is maintained in the isolated specific genomic region, identification of the interacting molecules and deduction of their functions are possible, and thus the method of the present invention is expected to greatly contribute to the analysis of molecular mechanisms of epigenetic regulation.

The identification of the interacting molecules in the isolated specific genomic region can be performed by an appropriate combination of known methods without particular limitation. This can be done, for example, by cancelling the maintained interaction, separating and purifying the interacting molecules, and then employing a known identification method. In the case where the treatment for maintaining the interaction is crosslinking with formaldehyde, the crosslinking can be reversed by addition of a high concentration salt solution (5 M NaCl solution etc.) and subsequent incubation at a suitable temperature for a suitable duration (for example, at about 65° C. overnight). Examples of the known identification method for proteins include mass spectrometry, immunoblot and ELISA (Enzyme-linked immunosorbent assay). Examples of the known identification method for DNA or RNA include base sequence analysis, microarray analysis and PCR (polymerase chain reaction).

<First Embodiment of Present Invention>

Figure 1:
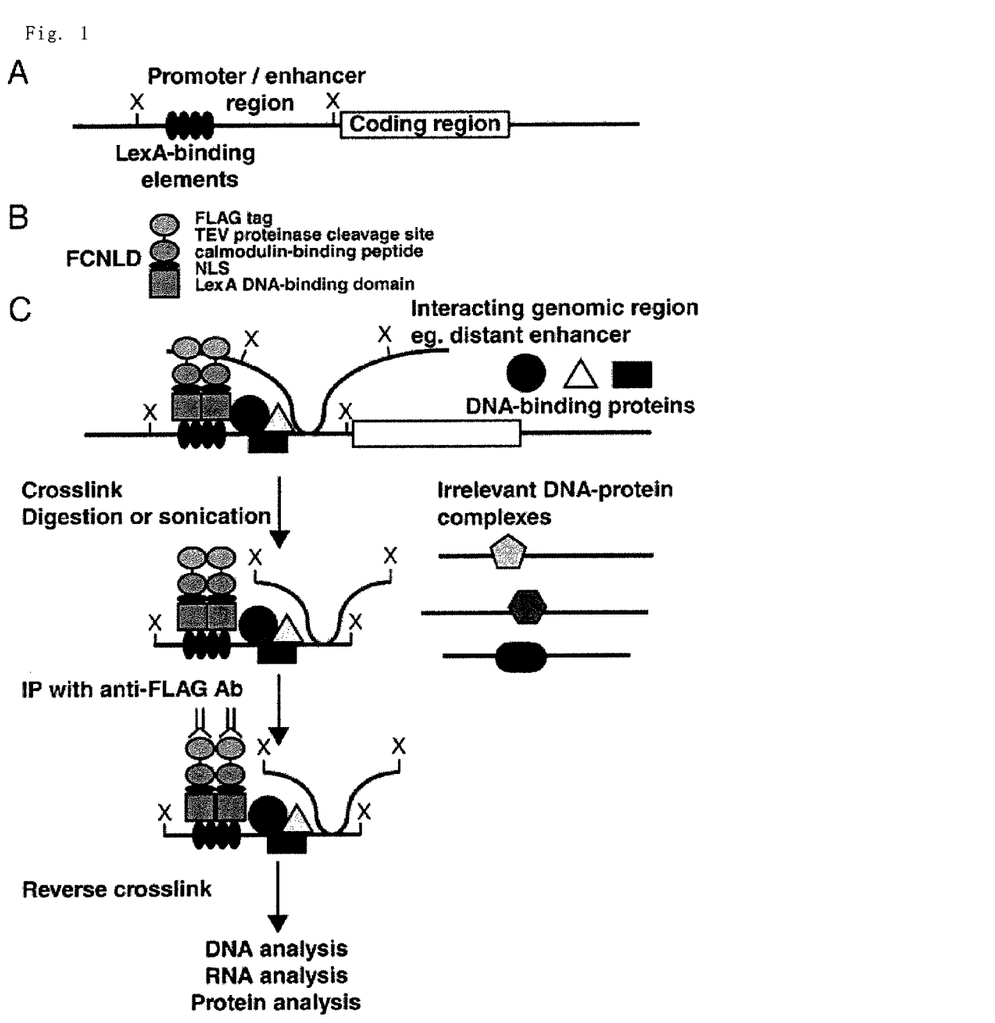
FIG. 1 shows the first embodiment of the method for isolating a specific genomic region according to the present invention.

A first embodiment of the present invention is shown in FIG. 1. However, the method of the present invention is not limited to this embodiment. In FIG. 1, X represents a restriction enzyme recognition site. Hereinafter, an embodiment of the present invention will be described according to FIG. 1.

(1) As shown in FIG. 1(A), a DNA having a sequence with several repeats of the LexA-binding element is inserted into a genomic region (shown as the promoter/enhancer region upstream of the coding region in FIG. 1(A)) of a cell to be analyzed.

(2) An expression vector for a fusion protein having the DNA-binding domain of a bacterial DNA-binding protein LexA linked to the nuclear localization signal of SV40 T antigen, a calmodulin-binding peptide, a TEV protease cleavage sequence and a FLAG tag (FCNLD, see FIG. 1(B)) is prepared, and then introduced into the cell to be analyzed so that the fusion protein can be expressed therein. Since the two kinds of tag sequences (FLAG tag and calmodulin-binding peptide) are linked to each other via the TEV protease cleavage sequence, two-step collection of a complex is possible.

(3) Stimulation is given to the prepared cell if needed. Next, the cell is subjected to crosslinking treatment with formaldehyde. By this treatment, interaction of the genomic DNA with proteins, RNA, DNA and other molecules in the genomic region to be isolated can be maintained. Of course, binding of FCNLD and the LexA-binding elements inserted in the genomic DNA can be also maintained (see the top of FIG. 1(C)).

(4) The cell is lysed and the crosslinked genomic DNA is digested with a restriction enzyme(s) into fragments (see the middle of FIG. 1(C)). Alternatively, fragmentation may be performed by sonication. By the treatment, DNA fragments having the inserted LexA-binding elements and DNA fragments without the LexA-binding elements ("irrelevant DNA-protein complexes" in the middle of FIG. 1(C)) are produced.

(5) The genomic region bound to the DNA-binding domain of LexA binds to an anti-FLAG antibody to form a complex (immunoprecipitated complex) (see the bottom of FIG. 1(C)).

(6) The complex, even after isolated, retains molecules interacting with the genomic region. Therefore, after crosslinking is reversed, proteins, RNA, DNA and other molecules can be purified and then identified.

<Second Embodiment of Present Invention>

Figure 11:
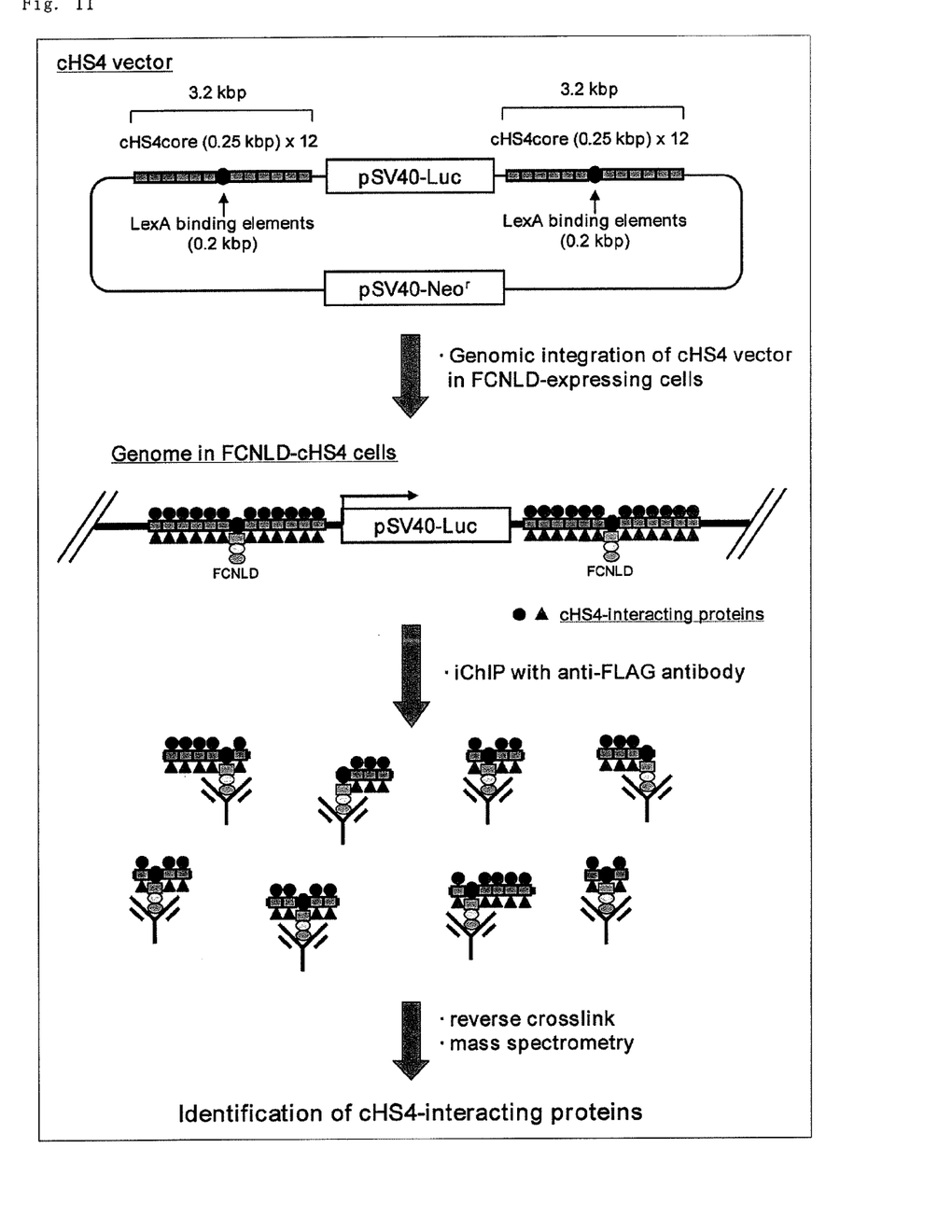
FIG. 11 shows the second embodiment of the method for isolating a specific genomic region according to the present invention.

A second embodiment of the present invention based on Example 3 is shown in FIG. 11. In FIG. 11, cHS4 core represents the specific genomic region used in Example 3, pSV40-Luc represents a reporter gene (luciferase) cassette, pSV40-Neo[r] represents a drug resistance (neomycin resistance) cassette. Hereinafter, the second embodiment of the present invention will be described according to FIG. 11.

(1) A vector having insertion of a DNA fragment having cHS4 core (specific genomic region) sequences and LexA-binding elements is prepared and then introduced into a cell. In the vector shown in FIG. 11 (cHS4 vector), the transgene is composed of a DNA fragment having six cHS4 core sequences in each side of the LexA-binding elements (12 cHS4 core sequences in total). One copy of the transgene is arranged in each side of pSV40-Luc. However, pSV40-Luc is not an essential component, and the cHS4 vector may carry only one transgene. A drug-resistance cassette is not essential, either, but preferably included in the cHS4 vector. In this case, cells having the transgene stably integrated in the genomic DNA can be selected by selecting neomycin resistant cells.

(2) In Example 3, since the transgenes have been introduced into a cell stably expressing FCNLD (see FIG. 1(B)), FCNLD binds to the LexA-binding elements in the transgenes integrated in the genome.

(3) After the cell, is subjected to crosslinking treatment with formaldehyde, restriction enzyme treatment or sonication is performed for fragmentation of the genomic DNA.

(4) The genomic region bound to the DNA-binding domain of LexA binds to an anti-FLAG antibody and thereby forms a complex (immunoprecipitated complex) therewith, which is then collected.

(5) After crosslinking in the collected complex is reversed, molecules interacting with the genomic region are identified by mass spectrometry etc.

<Kit>

The present invention provides a kit for isolating a specific genomic region. The kit of the present invention at least comprises either one of the following (A) and (B).

(A) A targeting vector for inserting a DNA fragment having a recognition sequence(s) for an exogenous DNA-binding molecule into genomic DNA (B) A vector for introducing, into a cell, a DNA fragment having a recognition sequence(s) for an exogenous DNA-binding molecule and a DNA sequence(s) of a specific genomic region Preferably, the kit further comprises an exogenous molecule at least having a DNA-binding domain of the exogenous DNA-binding molecule or an expression vector for the exogenous molecule. Other components of the kit are not particularly limited, and for example, a crosslinking reagent, a molecule capable of specifically binding to the exogenous molecule, a reaction tube(s), an instruction manual, etc. may be comprised in the kit. By use of the kit of the present invention, the method for isolating a specific genomic region according to the present invention can be simply and quickly performed.

As the exogenous DNA-binding molecule, exogenous DNA-binding molecules as described in the method for isolating a specific genomic region according to the present invention can be preferably used. In the case of a kit for isolating a specific genomic region of eukaryotic cells, the exogenous DNA-binding molecule is preferably LexA and particularly preferably FCNLD. It is preferable that the user of the kit can freely determine the homologous recombination region for the targeting vector of the above (A) and the specific genomic region in the vector of the above (B).

In the case where a functional DNA region such as a transcriptional regulatory DNA region is used as the specific genomic region in the above (B), the vector preferably comprises a reporter gene. Combination of a reporter gene and a functional DNA region such as a transcriptional regulatory DNA region enables confirmation of the level of interacting molecule-mediated functions such as transcriptional regulation. The reporter gene is not particularly limited and known reporter genes can be preferably used. Specific examples of the reporter gene include GFP (green fluorescent protein), luciferase and human CD2.

EXAMPLES

Hereinafter, the present invention will be illustrated in detail by examples, but is not limited thereto.

Example 1

(1) Preparation of FCNLD-BLG Cells

Figure 2:
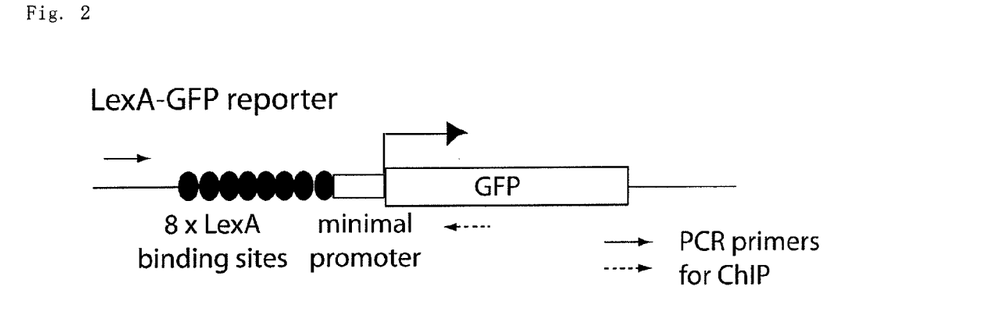
FIG. 2 shows the construct of the LexA-GFP reporter gene.

Experiments were performed using the BLG cell line (Literature I: Hoshino A. et al. Mol. Cell, 15, 153-159 (2004)). The BLG cell line is a cell line obtained by introduction of a LexA-GFP reporter gene having LexA-binding elements and a destabilized-GFP gene (see FIG. 2) into a mouse pro-B cell line, Ba/F3.

An expression plasmid for FCNLD (FCNLD/pEF) was introduced into the BLG cells, and thereby FCNLD-BLG cells were prepared. First, FCNLD/pEF was prepared in the following procedures.

(a) cDNA encoding the DNA-binding domain of LexA was amplified by PCR. For the PCR, the pLG plasmid (see the above-mentioned Literature I) was used as a template and the following primers 1 and 2 were used.

```
Primer 1:
                                  (SEQ ID NO: 1)
5'-ccctttcctgagggaatgaaagcgttaacg-3'

Primer 2:
                                  (SEQ ID NO: 2)
5'-tgcggccgcttagggttcaccggcagccac-3'
```

(b) The PCR product was digested with restriction enzymes (Bsu36I and NotI) and the digested fragment was ligated to the nuclear localization signal of SV40 T antigen in pBluescript (see the above-mentioned Literature I).

(c) The insert sequence was confirmed by DNA sequencing. Then, the obtained construct was digested with restriction enzymes (BamHI and NotI) and the digested fragment was subcloned into the pMIR-DFT vector. The pMIR-DFT vector is an expression vector for a fusion protein having two FLAG tags, a TEV protease recognition site and a calmodulin-binding peptide in the N-terminus.

(d) cDNA encoding FCNLD was excised from the obtained construct and then subcloned into pEF (Literature II: Fujii H. et al. Proc. Natl. Acad. Sci. USA, 92, 5482-5486 (1995)), and thereby FCNLD/pEF was obtained.

Figure 3:
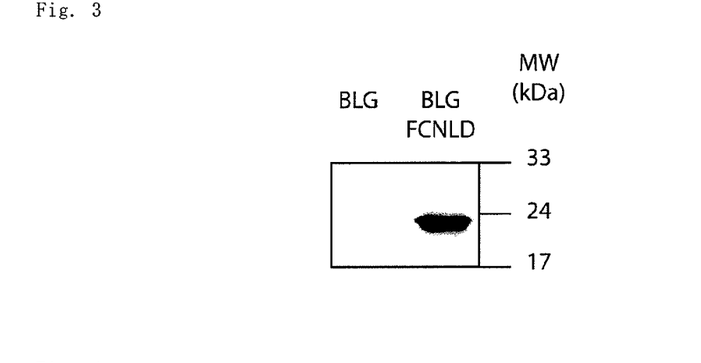
FIG. 3 shows the results of immunoblot analysis with the anti-LexA antibody, which confirm FCNLD expression in the FCNLD-BLG cells.

Expression of FCNLD in the FCNLD-BLG cells was confirmed by immunoblot analysis with an anti-LexA antibody (manufactured by Millipore, 06-719). FIG. 3 shows the results of the immunoblot analysis with the anti-LexA antibody on the extracts separately prepared from the parental BLG cells and the FCNLD-BLG cells. As shown in FIG. 3, expression of FCNLD in the FCNLD-BLG cells was confirmed.

(2) Isolation of the Specific Genomic Region

The isolation was performed using the parental BLG cells and the FCNLD-BLG cells in the following procedures.

(a) To 10 mL of an RPMI complete medium containing $2 \times 10^6$ cells, 270 μL of 37% formaldehyde was added and the mixture was allowed to stand at room temperature for 10 minutes. In this way, the cells were treated with formaldehyde for crosslinking. Next, for neutralization, 1 mL of a 1.25 M glycine solution was added and the mixture was allowed to stand at room temperature for 5 minutes.

(b) After centrifugation (at 1 krpm at room temperature for 5 minutes), the cells were washed twice with ice-cold PBS and then suspended in ice-cold PBS containing a protease inhibitor cocktail (Complete Mini, EDTA-free, manufactured by Roche).

(c) After centrifugation (at 700×g at 4° C. for 5 minutes), the pellets were suspended in 400 μL of SDS lysis buffer (50 mM Tris (pH 8.1), 10 mM EDTA, 1% SDS and a protease inhibitor cocktail).

(d) The crosslinked DNA was fragmented by sonication (sonicator: Cole Parmer, Ultra Sonic Processor, Model CP130; probe: CV18, 4273, amplitude 30, 10 sec×4 with 10 sec intervals).

(e) After centrifugation (at 10 krpm at 4° C. for 10 minutes), the supernatant was collected and then diluted with dilution buffer 1 (0.01% SDS, 1.1% Triton X-100, 1.2 mM EDTA, 16.7 mM Tris-HCl (pH 8.0), 167 mM NaCl and a protease inhibitor cocktail). Next, the reporter gene was immunoprecipitated with control IgG plus protein G-Sepharose (GE Healthcare), or with an anti-FLAG M2 affinity gel (Sigma Aldrich).

(f) After washing, the immunoprecipitated complex was subjected to elution with 200 μL of elution buffer (100 mM NaHCO$_3$ and 1% SDS).

(g) After addition of 8 μL of a 5 M NaCl solution, incubation was performed at 65° C. overnight and thereby crosslinking was reversed.

(h) After treatment with RNaseA and Proteinase K, DNA was purified.

(i) The resulting DNA was subjected to PCR and real-time PCR. For the PCR, the following primers 3 and 4 were used as primers for detection of the LexA-GFP reporter DNA (see FIG. 2).

```
Primer 3:
                                      (SEQ ID NO: 3)
5'-ccccagtgcaagtgcaggtgcc-3'

Primer 4:
                                      (SEQ ID NO: 4)
5'-cgtcgccgtccagctcgaccag-3'
```

Figure 4:
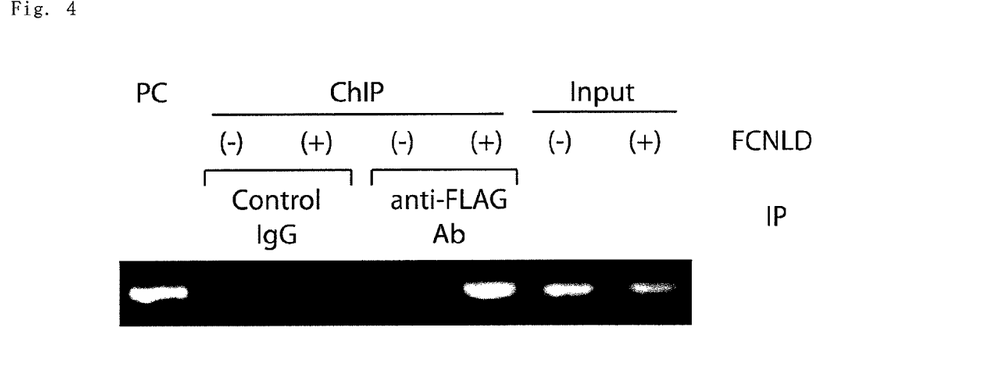
FIG. 4 shows the results of PCR detection of the LexA-GFP reporter DNA in the complex immunoprecipitated with the anti-FLAG antibody in Example 1.

The results of the PCR are shown in FIG. 4. In FIG. 4, PC represents a positive control sample containing a purified LexA-GFP reporter DNA as a PCR template and Input represents a sample obtained after the fragmented DNA was subjected to reverse of crosslinking without immunoprecipitation. FCNLD (−) represents a sample from the parental BLG cells, and FCNLD (+) represents a sample from the FCNLD-BLG cells. As is clear from FIG. 4, in comparison with the four samples obtained after immunoprecipitation, the LexA-GFP reporter DNA was detected only in the complex immunoprecipitated with the anti-FLAG antibody in the presence of FCNLD. In the samples obtained without immunoprecipitation (Input), the LexA-GFP reporter DNA was detected regardless of the presence of FCNLD. These results showed that by immunoprecipitation with the anti-FLAG antibody in the presence of FCNLD, the LexA-GFP reporter DNA can be recovered.

Figure 5:
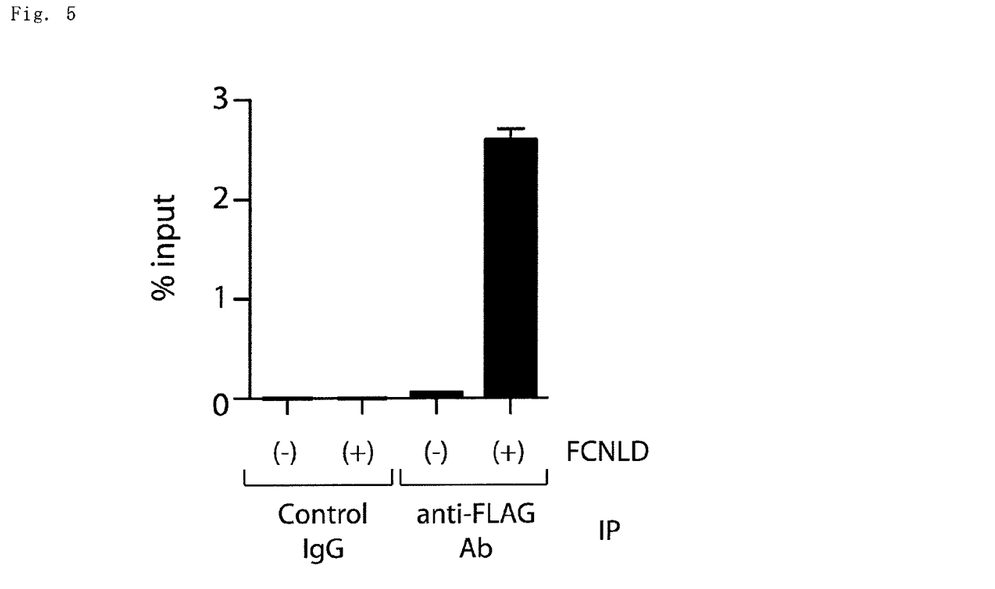
FIG. 5 shows the recovery ratio of the LexA-GFP reporter DNA in the complex immunoprecipitated with the control IgG or the anti-FLAG antibody in Example 1.

FIG. 5 shows the recovery ratio of the LexA-GFP reporter DNA in the immunoprecipitated complex. The recovery ratio was determined based on the amount of the LexA-GFP reporter DNA quantified by real-time PCR. In FIG. 5, "% input" of the vertical axis in the graph represents the ratio (recovery ratio) of the amount of the LexA-GFP reporter DNA recovered by the immunoprecipitation relative to the total amount of DNA after sonication. As shown in FIG. 5, by immunoprecipitation of the FCNLD-BLG cell-derived sample with the anti-FLAG antibody, about 2.5% of the LexA-GFP reporter DNA can be recovered.

These results demonstrate that the above-mentioned method enables isolation and recovery of specific genomic regions.

Example 2

(1) Preparation of FCNLD-BLIPG Cells

Figure 6:
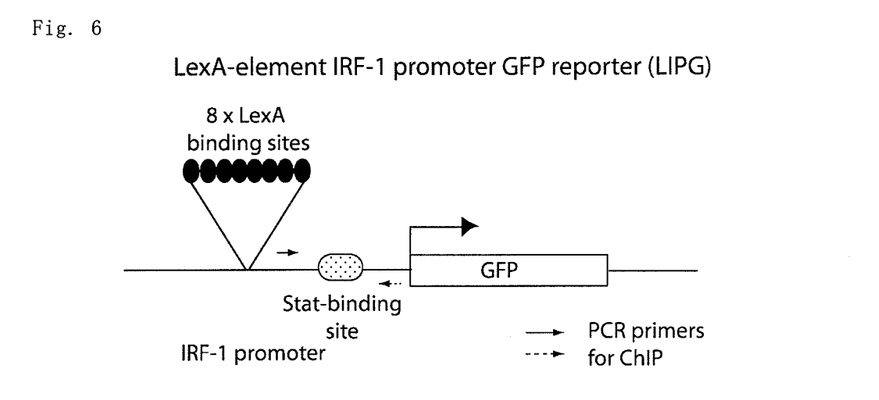
FIG. 6 shows the construct of the LexA-element IRF-1 promoter GFP reporter gene.

LexA-binding elements were inserted upstream of a Stat-binding sequence of human IRF-1 promoter and a GFP gene linked thereto, and thereby a LexA-element IRF-1 promoter GFP reporter (hereinafter referred to as "LIPG") gene was prepared (see FIG. 6). The Stat-binding sequence of human IRF-1 promoter is known to be essential for interferon-γ-induced transcription of IRF-1 gene (Literature III: Sims S H et al. Mol. Cell. Biol., 13, 690-702 (1993)). In addition, Stat1 is known to be necessary for interferon-γ-induced transcription of IRF-1 gene (Literature IV: Durbin J E et al. Cell, 84, 443-450 (1996); and Literature V: Meraz M A et al. Cell, 84, 431-442 (1996)).

The LIPG gene was stably transfected into Ba/F3 cells for preparation of a cell line, BLIPG. In turn, the FCNLD gene was stably transfected into the BLIPG cell line for preparation of a cell line, FCNLD-BLIPG. Expression of FCNLD in the FCNLD-BLIPG cells was confirmed by immunoblot analysis with the anti-LexA antibody.

(2) Interferon-γ-Induced Expression of GFP

Figure 7:
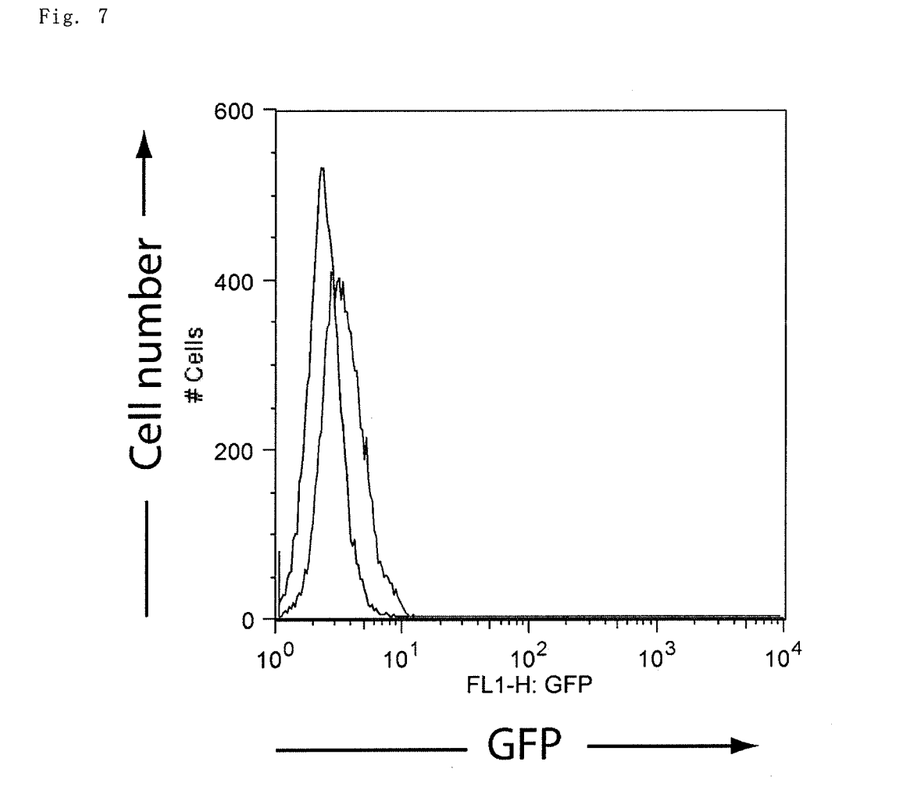
FIG. 7 shows the results of flow cytometry, which confirm GFP expression in the interferon-γ-stimulated FCNLD-BLIPG cells.

Interferon-γ-induced expression of GFP was confirmed by flow cytometry. This experiment was performed according to the method described in Literature VI: Hoshino A. et al. Biochem. Biophys. Res. Commun., 346, 1062-1066 (2006). The results are shown in FIG. 7. As shown in FIG. 7, where the graph is shifted to the right by addition of interferon-γ, expression of GFP was confirmed.

(3) Immunoprecipitation with Anti-Stat1 Antibody

After addition of 10 ng/mL interferon-γ, 2×10$^7$ of the FCNLD-BLIPG cells were incubated for 15 or 30 minutes. A control without addition of interferon-γ was prepared for the experiment. In the same manner as in the above (2) (a) to (h) of Example 1, the cells were treated with formaldehyde for crosslinking and lysed, and fragmentation by sonication, immunoprecipitation, reverse of crosslinking and DNA purification were performed. The immunoprecipitation was performed using an anti-Stat1 antibody.

The purified DNA was subjected to PCR. For the PCR, the following primers 5 and 6 were used as primers for detection of LIPG (see FIG. 6).

```
Primer 5:
                                      (SEQ ID NO: 5)
5'-tgtacttccccttcgccgctagct-3'

Primer 6:
                                      (SEQ ID NO: 6)
5'-gcaatccaaacacttagcgggatt-3'
```

Figure 8:
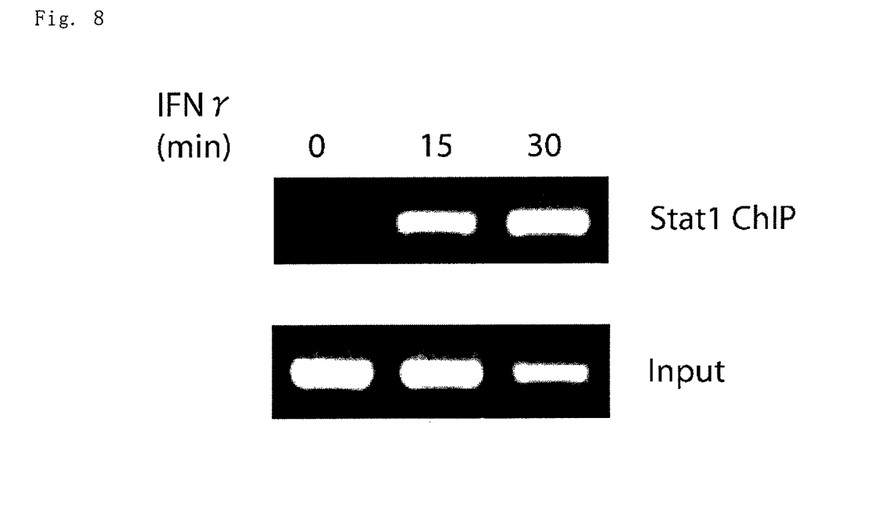
FIG. 8 shows the results of PCR detection of LIPG in the complex immunoprecipitated with the anti-Stat1 antibody in Example 2.

The results are shown in FIG. 8. In FIG. 8, the sample shown as "IFNγ at 0 min" represents a control without addition of interferon-γ. Input represents a sample obtained after the fragmented DNA was subjected to reverse of crosslinking without immunoprecipitation. As is clear from FIG. 8, LIPG was detected in the immunoprecipitated complexes of the anti-Stat1 antibody and the DNA fragment obtained from the interferon-γ-treated FCNLD-BLIPG cells, while LIPG was not detected in the immunoprecipitated complex derived from the interferon-γ non-treated cells. In the samples obtained without immunoprecipitation (Input), LIPG was detected regardless of the presence of interferon-γ treatment.

These results demonstrate that interferon-γ treatment of the FCNLD-BLIPG cells enables binding of Stat1 to LIPG and isolation of LIPG using the anti-Stat1 antibody.

(4) Immunoprecipitation with Anti-Flag Antibody

After addition of 10 ng/mL interferon-γ, $1\times10^8$ of the FCNLD-BLIPG cells were incubated for 30 minutes. A control without addition of interferon-γ was prepared for the experiment. In the same manner as in the above (2) (a) to (h) of Example 1, the cells were treated with formaldehyde for crosslinking and lysed, and fragmentation by sonication, immunoprecipitation, reverse of crosslinking and DNA purification were performed.

Specifically, the immunoprecipitation was performed using control IgG plus protein G-Sepharose, or using an anti-FLAG M2 affinity gel. PCR was performed using the purified DNA as a template and the above-mentioned primers 5 and 6. Similarly, PCR was performed on the samples obtained without immunoprecipitation (Input).

Figure 9:
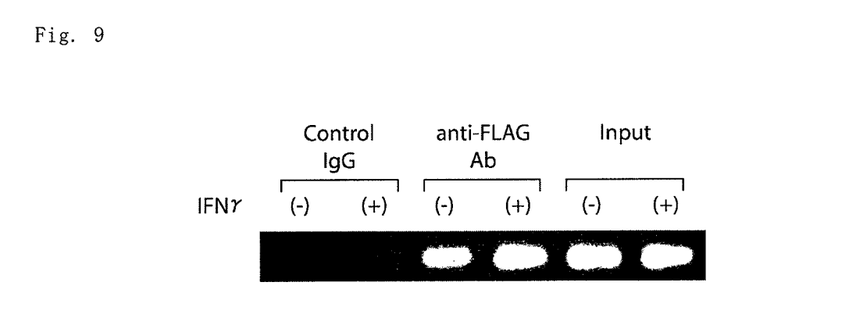
FIG. 9 shows the results of PCR detection of LIPG in the complex immunoprecipitated with the anti-FLAG antibody in Example 2.

The results are shown in FIG. 9. In FIG. 9, IFNγ (−) represents an interferon-γ non-treated sample, and IFNγ (+) represents an interferon-γ-treated sample. As is clear from FIG. 9, LIPG was not detected in the complexes immunoprecipitated with control IgG, but LIPG was detected in the complexes immunoprecipitated with the anti-FLAG antibody regardless of the presence of interferon-γ treatment. Needless to say, in the samples obtained without immunoprecipitation (Input), LIPG was detected regardless of the presence of interferon-γ treatment.

These results demonstrate that LIPG can be isolated by use of the anti-FLAG antibody.

(5) Two-Step Immunoprecipitation with Anti-Flag Antibody and Anti-Stat1 Antibody After addition of 10 ng/mL interferon-γ, $1\times10^8$ of the FCNLD-BLIPG cells were incubated for 30 minutes. A control without addition of interferon-γ was prepared for the experiment. In the same manner as in the above (2) (a) to (e) of Example 1, the cells were treated with formaldehyde for crosslinking and lysed, and fragmentation by sonication and immunoprecipitation were performed. For the first step of immunoprecipitation, an anti-FLAG M2 affinity gel was used.

Next, the immunoprecipitated complex was incubated with 1000 units of AcTEV protease (Invitrogen) at 30° C. for 3 hours. As a result of the step, FCNLD bound to the LexA-binding elements of LIPG was cleaved to release LIPG from the anti-FLAG M2 affinity gel. The second step of immunoprecipitation was performed on the released LIPG using protein G-Sepharose plus control IgG or protein G-Sepharose plus an anti-Stat1 antibody. After this, reverse of crosslinking and DNA purification were performed according to the procedures of Example 1.

PCR was performed using the purified DNA as a template and the above-mentioned primers 5 and 6. Similarly, PCR was performed on the samples obtained without immunoprecipitation (Input) and the samples obtained after the AcTEV protease treatment (without the second step of immunoprecipitation).

Figure 10:
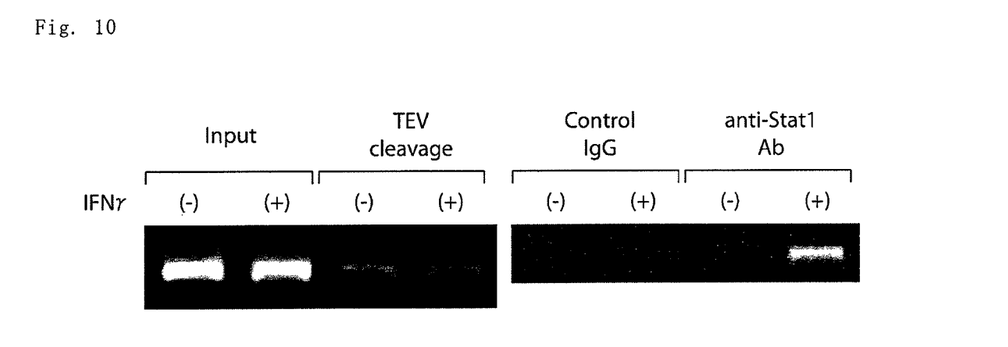
FIG. 10 shows the results of PCR detection of LIPG in the complex obtained by two-step immunoprecipitation with the anti-FLAG antibody and the anti-Stat1 antibody in Example 2.

The results are shown in FIG. 10. In the samples obtained without immunoprecipitation (Input), LIPG was detected regardless of the presence of interferon-γ treatment. Also, in the samples obtained after the AcTEV protease treatment, LIPG was detected regardless of the presence of interferon-γ treatment. In the case where the second step of immunoprecipitation was performed, LIPG was detected in the second immunoprecipitated complex only when the interferon-γ treatment was performed and the anti-Stat1 antibody was used.

These results demonstrate that chromatin complexes containing transcription factors activated by extracellular signals can be isolated and provided for biochemical and molecular biological analysis.

Example 3

An insulator, which is constituted by an insulator sequence in the genome and molecules capable of binding thereto, exhibits an enhancer blocking effect and protects genes against position effects, and thereby enables coordinated expression of tens of thousands of genes without interference (Chung, J. H., Bell, A. C. and Felsenfeld, G., Characterization of the chicken beta-globin insulator, Proc. Natl. Acad. Sci. U.S.A. 94 (2), 575-580 (1997); and Burgess-Beusse B, Farrell C, Gaszner M, Litt M, Mutskov V, Recillas-Targa F, Simpson M, West A, Felsenfeld G. The insulation of genes from external enhancers and silencing chromatin. Proc. Natl. Acad. Sci. U.S.A. 99 (10), 16433-16437 (2002)). Identification of insulator-binding proteins was attempted using the method for isolating a specific genomic region according to the present invention.

(1) Preparation of FCNLD-cHS4 Cells

The core sequences of the cHS4 sequence known as an insulator sequence of the chicken globin gene were tandemly linked and inserted into two sites (12 sequences each), namely the upstream and downstream of the luciferase (Luc) gene of the reporter vector pGL3-Control (Promega). In the two sites, LexA-binding elements were inserted into the center of the tandemly-linked cHS4 core sequences to give a cHS4 vector (see FIG. 11). The cHS4 nucleotide sequence is registered with DDBJ/GenBank/EMBL as accession number: U78775, and the region of positions 1 to 244 thereof corresponds to the core sequence.

The FCNLD gene was stably transfected into a cell line, Ba/F3, for preparation of a cell line, FCNLD, and in turn, the cHS4 vector was stably transfected into the FCNLD cell line for preparation of a cell line, FCNLD-cHS4. Also, the pGL3-Control vector was stably transfected into the FCNLD cell line for preparation of a cell line, FCNLD-pGL3C, as a negative control.

(2) Immunoprecipitation with Anti-Flag Antibody

The cHS4 region was isolated in the following procedures by use of the FCNLD-cHS4 cells and the FCNLD-pGL3C cells.

(I) To 45 mL of an RPMI complete medium containing $4\times10^7$ cells, 1.2 mL of 37% formaldehyde was added and the mixture was allowed to stand at 37° C. for 5 minutes. In this way, the cells were treated with formaldehyde for crosslinking. Next, for neutralization of formaldehyde, 4.5 mL of a 1.25 M glycine solution was added and the mixture was allowed to stand at room temperature for 5 minutes.

(II) The cells were washed and collected in the same manner as (2) (b) of Example 1.

(III) The cell pellets were suspended in 20 mL of cytoplasmic lysis buffer (10 mM Tris (pH 8.0), 1 mM EDTA, 0.5% NP-40 and a protease inhibitor cocktail) and then placed on ice for 10 minutes. After centrifugation (at 2,000 rpm at 4° C. for 8 minutes), the precipitates were suspended in 20 mL of nuclear lysis buffer (10 mM Tris (pH 8.0), 1 mM EDTA, 0.5 M NaCl, 1% Triton X-100, 0.5% sodium deoxycholate, 0.5% sarcosyl and a protease inhibitor cocktail) and then placed on ice for 10 minutes. After centrifugation (at 2,000 rpm at 4° C. for 8 minutes), the precipitates were washed twice with ice-cold PBS to give a chromatin fraction.

(IV) The chromatin fraction was suspended in 1.6 mL of lysis buffer (10 mM Tris (pH 8.0), 1 mM EDTA, 0.5 mM EGTA, 150 mM NaCl, 0.1% sodium deoxycholate and 0.1% SDS) and the suspension was poured in a volume of 0.8 mL each into 1.5 mL microtubes. The chromatin fraction was subjected to fragmentation by sonication (sonicator: TOMY UD-200, microtip probe TP-040, <conditions per tube> output 3, a set of 10-sec ultrasound generation and subsequent 50-sec ice-cooling×18 times). After centrifugation (at 15,000 rpm at 4° C. for 10 minutes), the supernatants were collected.

(V) To the fragmented chromatin (1.6 mL), a normal mouse IgG and protein G-Dynabeads (VERITAS) were added, and the mixture was rotated at 4° C. for 1 hour. To the supernatant, an anti-FLAG antibody (Wako Pure Chemical Industries, Ltd.) and protein G-Dynabeads (VERITAS) were added, and the mixture was rotated at 4° C. overnight for immunoprecipitation of the cHS4 region.

(VI) After washing, 50 μL of 2×SDS sample buffer was added to the immunoprecipitated complex, and the mixture was heated at 98° C. for 20 minutes.

(3) Identification of cHS4 Core Sequence-Binding Proteins by Mass Spectrometry

Figure 12:
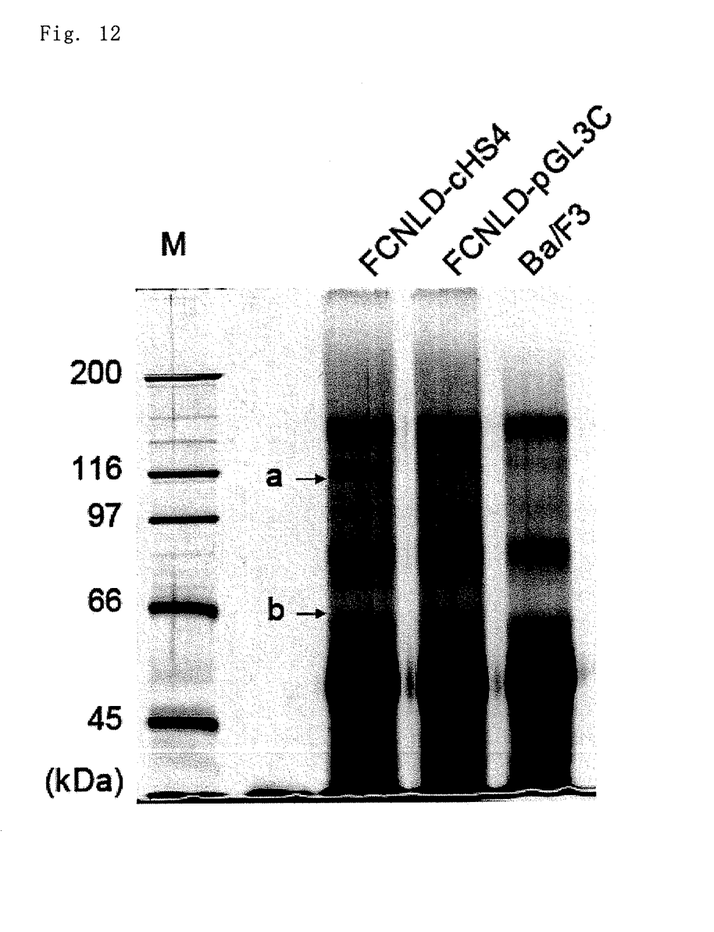
FIG. 12 shows detection of proteins specifically binding to the cHS4 core in the complex immunoprecipitated with the anti-FLAG antibody by SDS polyacrylamide gel electrophoresis (SDS-PAGE) and silver staining in Example 3.

The immunoprecipitates were subjected to SDS-PAGE, and after this, silver staining was performed for protein detection. The results are shown in FIG. 12. As is clear from FIG. 12, the bands a and b were detected in the immunoprecipitates derived from the FCNLD-cHS4 cells but not from the FCNLD-pGL3C cells (negative control). The bands a and b were excised and subjected to mass spectrometry. The results showed that the bands a and b correspond to novel cHS4 core sequence-binding proteins (proteins a and b).

These results demonstrate that proteins capable of specifically binding to the sequence of a specific genomic region can be isolated as a chromatin complex and identified by mass spectrometry.

(4) Confirmation of Binding of Novel cHS4 Core Sequence-Binding Proteins to cHS4 Region Binding of novel cHS4 core sequence-binding proteins a and b to the cHS4 region was confirmed by chromatin immunoprecipitation. Specifically, chromatin immunoprecipitation with an anti-a antibody or an anti-b antibody was performed on the FCNLD-cHS4 cell-derived fragmented chromatin prepared in the above (2). Then, reverse of crosslinking in the immunoprecipitated complex and DNA purification were performed. The purified DNA was subjected to PCR. For the PCR, the following primers 7 and 8 were used as primers for detection of the region containing LexA-binding elements flanked by the cHS4 core sequences (see the bottom of FIG. 13).

```
Primer 7:
                                          (SEQ ID NO: 7)
5'-ttctctatcgataggtacctcg-3'

Primer 8:
                                          (SEQ ID NO: 8)
5'-tctattcagcggatctcgagcg-3'
```

Figure 13:
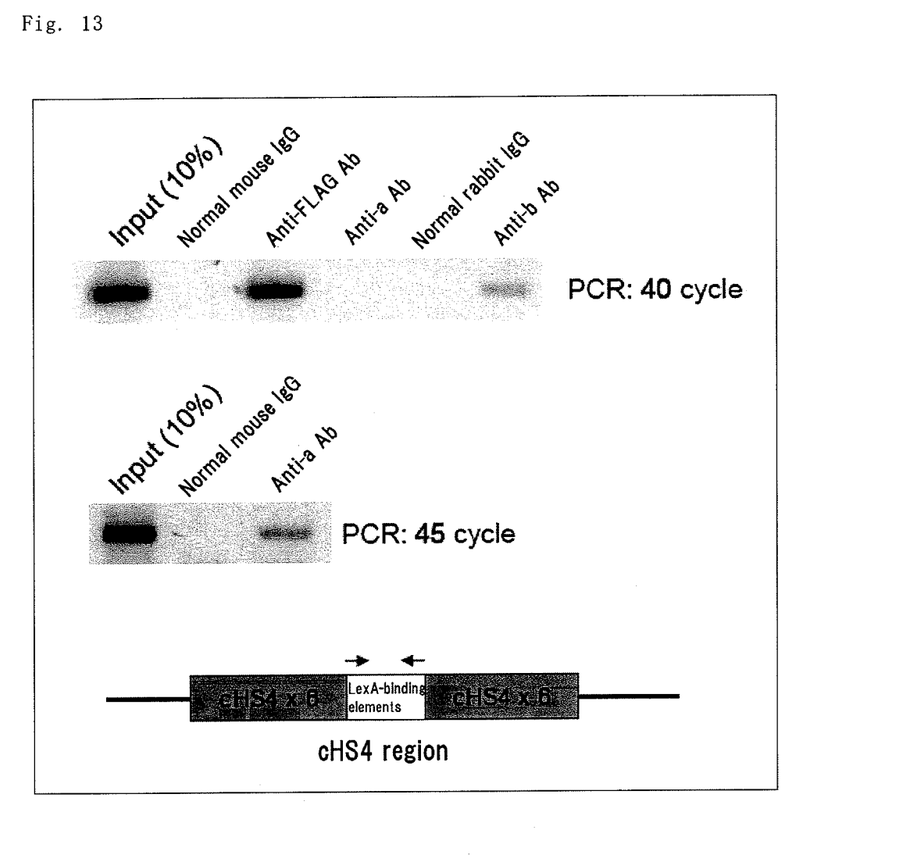
FIG. 13 shows the results of PCR detection of the cHS4 core-flanked LexA-binding element region in the complex immunoprecipitated with the anti-a antibody or the anti-b antibody in Example 3.

The results are shown in FIG. 13. In FIG. 13, Input represents a sample obtained after the fragmented DNA was subjected to reverse of crosslinking without immunoprecipitation. Other signs represent the respective antibodies used for immunoprecipitation. As shown at the top of FIG. 13, the objective DNA region was detected in the complex immunoprecipitated with the anti-b antibody in the case of 40-cycle PCR. In the complex immunoprecipitated with the anti-a antibody, the objective DNA region was not detected after 40 cycles of PCR, but detected after 45 cycles of PCR as shown in the middle of FIG. 13. These results confirmed binding of proteins a and b to the cHS4 region.

The present invention is not limited to the aforementioned embodiments and examples, and various modifications can be made within the scope of the appended claims. Other embodiments obtainable by suitably combining technical means disclosed in different embodiments of the present invention are also included in the technical scope of the present invention. All the academic publications and patent literature cited in the above description are incorporated herein by reference.

---

The invention claimed is:

1. A method for isolating a specific genomic region while maintaining interaction of the specific genomic region with its interacting molecule(s), the method comprising the steps 1 to 5:

step 1:
preparing a cell in which a DNA fragment having a recognition sequence(s) for an exogenous DNA-binding molecule is inserted in genomic DNA of a genomic region to be isolated;

step 2:
bringing genomic DNA of the cell into contact with an exogenous molecule at least having a DNA-binding domain of the exogenous DNA-binding molecule;

step 3:
performing a treatment for maintaining interaction of the genomic DNA of the cell with a molecule(s) interacting with the genomic DNA;

step 4:
performing a treatment for fragmenting the genomic DNA; and step 5:
allowing a complex to be formed by binding of a molecule capable of specifically binding to the exogenous molecule, and then collecting the complex.

2. The method according to claim 1, wherein the exogenous DNA-binding molecule is an exogenous DNA-binding protein or an exogenous nucleic acid.

3. The method according to claim 1, wherein the exogenous molecule is a fusion molecule having a tag sequence(s).

4. The method according to claim 3, wherein the fusion molecule has two kinds of tag sequences linked to each other via a protease recognition sequence.

5. The method according to claim 1, wherein the exogenous molecule is a fusion molecule having a nuclear localization signal(s).

6. The method according to claim 1, wherein the DNA fragment having a recognition sequence(s) for an exogenous DNA-binding molecule is inserted into the genomic DNA by homologous recombination in step 1.

7. The method according to claim 1, wherein a DNA fragment having a recognition sequence(s) for an exogenous DNA-binding molecule and a DNA sequence(s) of a specific genomic region is introduced into a cell in step 1.

8. The method according to claim 1, wherein, in step 2, a gene encoding the exogenous molecule is introduced into the cell prepared in step 1, for expression of the gene in the cell.

9. The method according to claim 1, wherein the treatment for maintaining the interaction is crosslinking.

10. The method according to claim 1, wherein the treatment for fragmenting the genomic DNA is restriction enzyme treatment, partial degradation treatment with deoxyribonuclease, or sonication.

11. A kit for isolating a specific genomic region, comprising a targeting vector for inserting, into genomic DNA, a DNA fragment having a recognition sequence(s) for an exogenous DNA-binding molecule.

12. A kit for isolating a specific genomic region, comprising a vector for introducing, into a cell, a DNA fragment having a recognition sequence(s) for an exogenous DNA-binding molecule and a DNA sequence(s) of a specific genomic region.

13. The kit according to claim 12, wherein the DNA fragment further has a reporter gene.

14. The kit according to claim 11, further comprising an exogenous molecule at least having a DNA-binding domain of the exogenous DNA-binding molecule, or an expression vector for the exogenous molecule.

\* \* \* \* \*